United States Patent [19]
Sprecker

[11] Patent Number: 4,614,611
[45] Date of Patent: Sep. 30, 1986

[54] ORGANOLEPTIC USES OF PARA-METHYLACETOPHENONE DIMETHYLACETAL

[75] Inventor: Mark A. Sprecker, Sea Bright, N.J.

[73] Assignee: International Flavors & Fragrances Inc., New York, N.Y.

[21] Appl. No.: 698,861

[22] Filed: Feb. 6, 1985

[51] Int. Cl.[4] ........................... A61K 7/46; C11B 9/00
[52] U.S. Cl. ................................. 252/522 R; 252/8.6; 252/174.11; 252/522 A
[58] Field of Search .................... 568/592; 252/522 R, 252/522 A, 174.11, 8.6

[56] References Cited

PUBLICATIONS

Sigmund et al, Chemical Abstracts, vol. 23 (1929) 2416–2417.
Jour. Amer. Chem. Soc., 96 (1974) 467.

*Primary Examiner*—Bernard Helfin
*Attorney, Agent, or Firm*—Arthur L. Liberman

[57] ABSTRACT

Described is the para-methylacetophenone dimethylacetal having the structure:

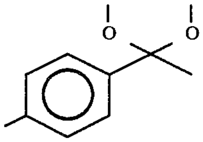

and organoleptic uses thereof for augmenting or enhancing the aroma of perfume compositions, perfumed articles, colognes and perfumed polymers.

4 Claims, 2 Drawing Figures

FIG.I

NMR SPECTRUM FOR FRACTION 7 OF EX. I

IR SPECTRUM FOR FRACTION 7 OF EXAMPLE I

ORGANOLEPTIC USES OF PARA-METHYLACETOPHENONE DIMETHYLACETAL

BACKGROUND OF THE INVENTION

This invention relates to the para-methylacetophenone dimethylacetal having the structure:

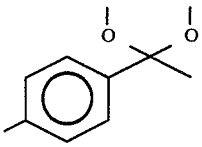

and organoleptic uses thereof in augmenting or enhancing the aroma of perfume compositions, colognes, perfumed articles and perfumed polymers.

Chemical compounds which can provide sweet, animalic, musky and licorice aromas with floral, basil and ylang topnotes are highly desirable in the art of perfumery and in the art of detergent manufacture and fabric softener manufacture. Many of the natural materials which provide such fragrance nuances are high in cost, vary in quality from one batch to another and/or are generally subject to the usual variations of natural products.

There is, accordingly, a continuing effort to find synthetic materials which will aid in replacing, enhancing or augmenting the essential fragrance notes provided by natural musks, basil and ylang. Unfortunately, many of the synthetic materials either have the desired nuances only to a relatively small degree or else contribute undesirable or unwanted odor to the compositions.

Phenyl substituted acetals are known to be useful in the art of perfumery, for example, the phenyl alkenyl acetals of U.S. Pat. No. 3,922,237 issued Nov. 25, 1975.

The dimethyl ketal of acetophenone having the structure:

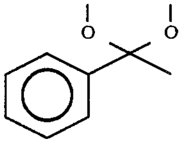

is a known compound produced according to the reaction:

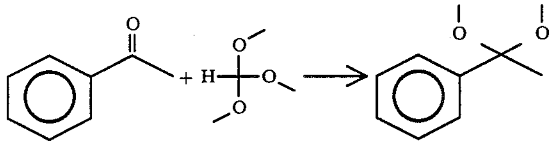

according to Taylor, et al, Synthesis (7), 467, (1977), abstracted at Chem. Abstracts, Volume 87, No. 133229z.

The para-methylacetophenone dimethylacetal of my invention having the structure:

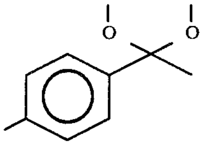

has unobvious, unexpected and advantageous organoleptic properties when compared with the organoleptic properties of the compound having the structure:

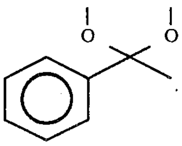

BRIED DESCRIPTION OF THE DRAWINGS

Figure 1:
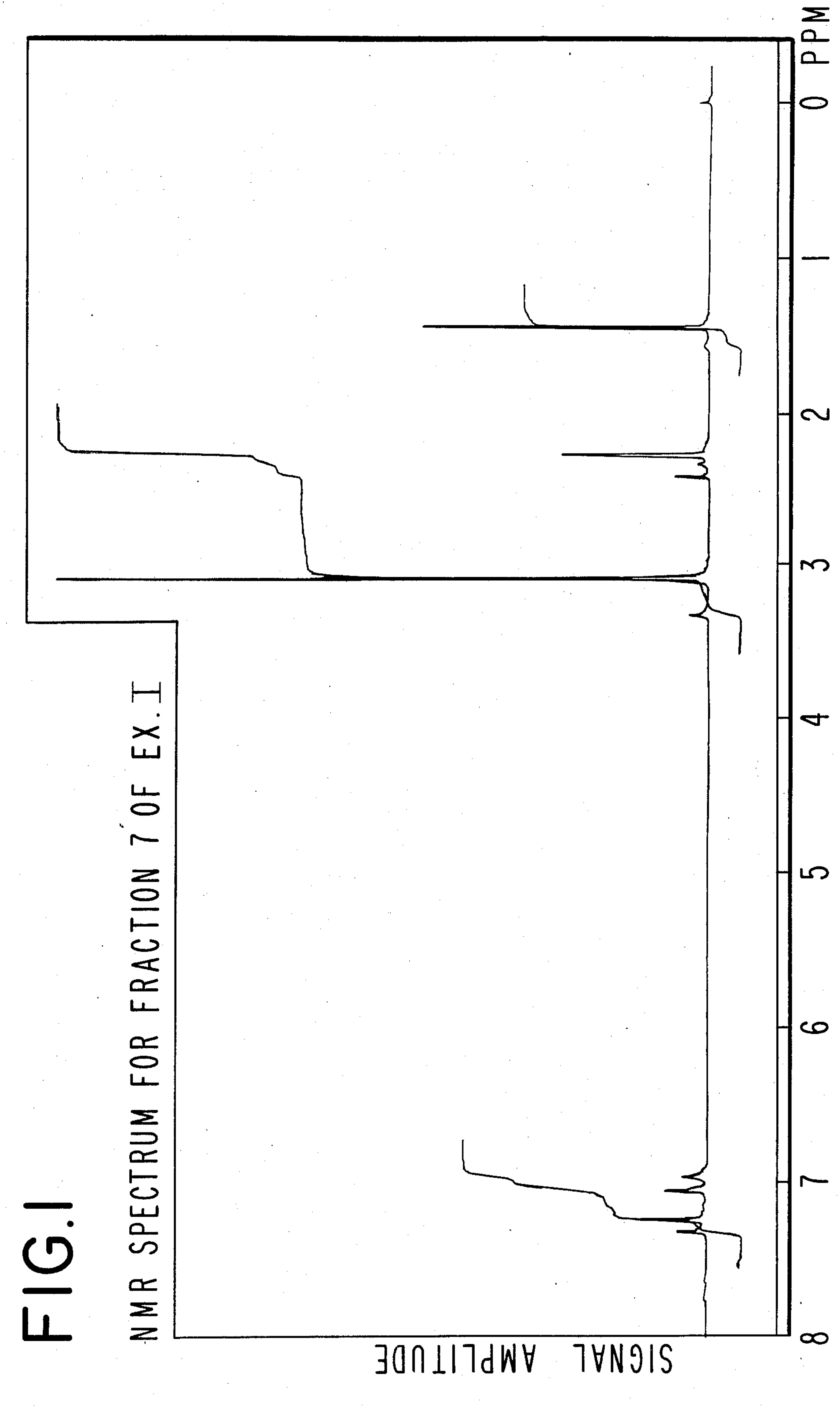

FIG. 1 is the NMR spectrum for fraction 7 of the distillation of the reaction product of Example I containing the compound having the structure:

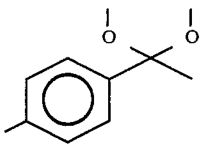

(Conditions: Field strength: 100 MHz; solvent: $CFCl_3$).

Figure 2:
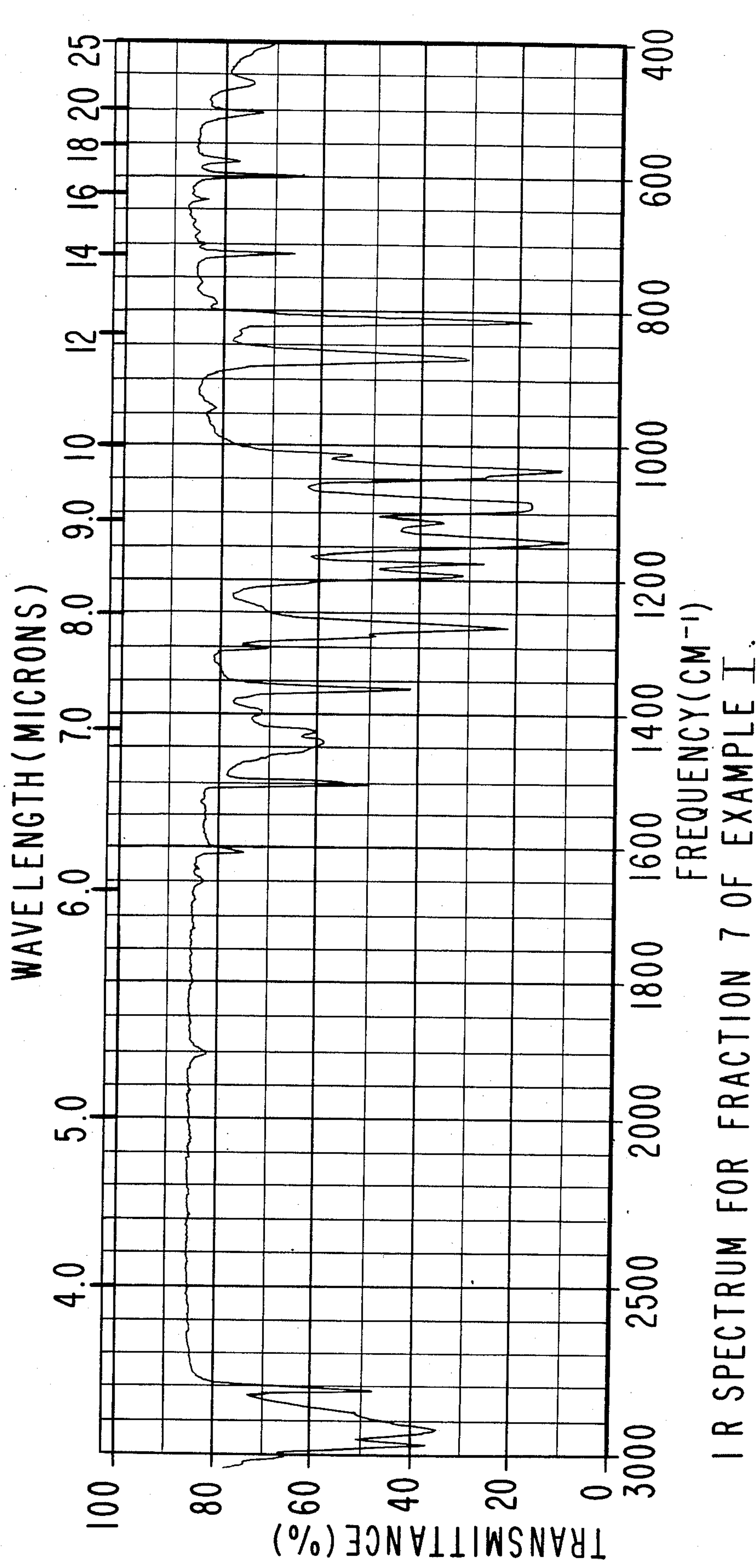

FIG. 2 is the infra-red spectrum for fraction 7 of the distillation of the reaction product of Example I containing the compound having the structure:

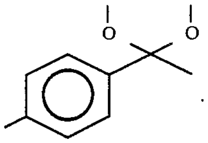

THE INVENTION

This invention relates to the para-methylacetophenone dimethylacetal having the structure:

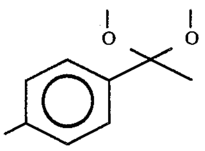

as well as organoleptic uses of said para-methylacetophenone dimethylacetal in augmenting or enhancing the aroma of perfumes, colognes, perfumed polymers and perfumed articles such as anionic, cationic, nonionic and zwitterionic solid or liquid detergents, fabric softeners such as drier added fabric softener articles and fabric softener compositions as well as deodorant compositions.

The para-methylacetophenone dimethylacetal of my invention having the structure:

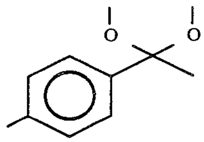

augments or enhances sweet, animalic, musky and licorice aromas with floral, basil and ylang topnotes of perfume compositions, colognes, perfumed polymers and perfumed articles.

The para-methylacetophenone dimethylacetal of my invention having the structure:

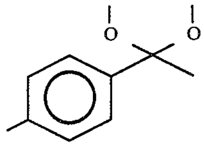

can be prepared by reacting para-methylacetophenone with trimethyl orthoformate according to the reaction:

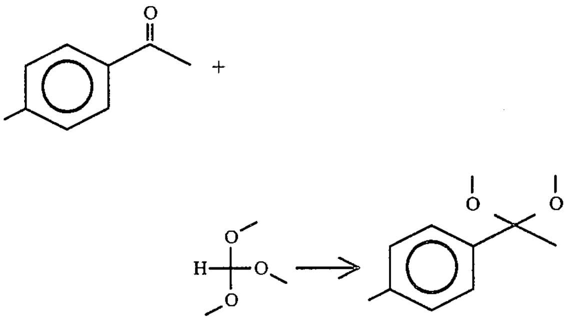

according to the procedure of Taylor, et al, Synthesis (7), 467, (1977), abstracted at Chem. Abstracts, Volume 87, No. 133229z the disclosures for which are incorporated by reference herein.

The reaction:

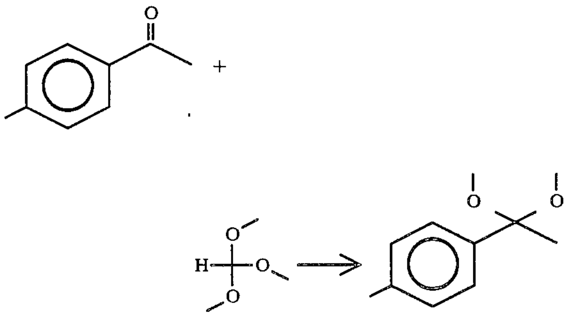

may be carried out in the presence of an acid such as hydrochloric acid and in the presence of a methanol solvent. At the end of the reaction, the reaction mass is neutralized with a base, for example, sodium carbonate and washed with water. The organic layer is distilled using a fractional distillation column to yield the compound having the structure:

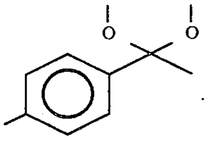

As stated, supra, the para-methylacetophenone dimethylacetal of my invention can be used to contribute an intense, long lasting, sweet, animalic, musky, licorice aroma with floral, basil and ylang topnotes to perfumes, perfumed articles, colognes and perfumed polymers. Examples of perfumed articles are anionic, cationic, nonionic and zwitterionic solid or liquid detergents, fabric softeners including drier-added fabric softener articles, fabric softener compositions, hair preparations and cosmetic powders. As olfactory agents, the para-methylacetophenone dimethylacetal of my invention can be formulated into or used as a component of a "perfume composition" or can be used as a component of a "perfumed article" or the perfume composition may be added to "perfumed articles".

The term "perfume composition" is used herein to mean a mixture of organic compounds including, for example, alcohols, aldehydes, ketones, nitriles, ethers, lactones, acetals, ketals other than the ketal of my invention, natural essential oils, synthetic essential oils and frequently hydrocarbons which are admixed so that the combined odors of the individual components produce a pleasant or a desired fragrance. Such perfume compositions usually contain: (a) the main note or "bouquet" or foundation stone of the composition; (b) modifiers which round off and accompany the main note; (c) fixatives, which include odorous substances which lend a particular note to the perfume throughout all stages of evaporation, and substances which retard evaporation; and (d) topnotes which are usually low boiling fresh smelling materials.

In perfume compositions the individual component will contribute its particular olfactory chracteristics, but the overall effect of the perfume composition will be the sum of the effects of each of the ingredients. Thus, the para-methylacetophenone dimethylacetal of this invention can be used to alter the aroma characteristics of a perfume composition, for example, by highlighting or moderating the olfactory reaction contributed by another ingredient in the composition.

The amount of the para-methylacetophenone dimethylacetal of my invention which will be effective in perfume compositions depends on many factors including the other ingredients, their amounts and the effects which are desired. It has been found that perfume compositions containing as little as 0.5% of the para-methylacetophenone dimethylacetal of my invention or even less can be used to impart or augment interesting, substantive and long lasting, sweet, animalic, musky and licorice aromas with floral, basil and ylang topnotes to soaps, liquid and solid cationic, nonionic, anionic and zwitterionic detergents, cosmetic powders, liquid and solid fabric softeners, drier added fabric softener articles, optical brightener compositions and other products. The amount employed can range up to 50% or more and will depend on considerations of cost, nature of the end product and the effect desired on the finished product and particular fragrance sought.

The para-methylacetophenone dimethylacetal of my invention can be used alone or in a perfume composition as an olfactory component in detergents, soaps, space odorants and deodorants; perfumes; colognes; toilet waters; bath salts; hair preparations, such as lacquers, brilliantines, pomades and shampoos; cosmetic preparations, such as creams, deodorants, hand lotions and sun screens; powders, such as talcs, dusting powders, face powders and the like. When used as an olfactory component of a perfumed article such as a cationic, nonionic, anionic or zwitterionic solid or liquid detergent, as little as 0.01% of the para-methylacetophenone dimethylacetal based on the overall weight of the article will suffice to impart interesting, long lasting and substantive, sweet, animalic, musky and licorice aromas with floral, basil and ylang topnotes. Generally, no more than 0.9% is required. Accordingly, the range of use of the para-methylacetophenone dimethylacetal of my invention in perfumed articles is from about 0.01% up to about 0.9% based on the weight of the perfumed article.

In addition, the perfume composition can contain a vehicle or carrier for the para-methylacetophenone dimethylacetal alone or along with other ingredients. The vehicle can be a liquid such as a non-toxic alcohol such as ethanol, a glycol such as propylene glycol or the like. The carrier can be an absorbent solid such as a gum (e.g., guar gum, xanthan gum and the like) or components for encapsulating the compositions such as gelatin which can be used to form a capsule wall surrounding the perfume oil as by means of coacervation.

The following Example I serves to illustrate the method for manufacture of the para-methylacetophenone dimethylacetal of my invention. Examples II, et seq, serve to illustrate the organoleptic uses of the para-methylacetophenone dimethylacetal of my invention. This invention is to be considered restricted thereto only as indicated in the appended claims.

All parts and percentages given herein are by weight unless otherwise specified.

EXAMPLE I

Preparation of Para-Methylacetophenone Dimethylacetal

Reaction:

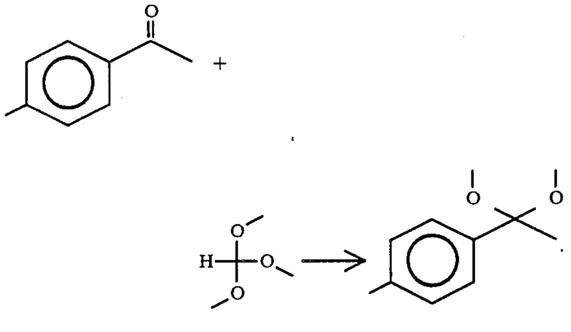

Into a 5 liter reaction flask equipped with stirrer, thermometer, reflux condenser, addition funnel, gas dispersion tube and cooling bath is placed 730 grams of para-methylacetophenone and 915 grams of trimethyl orthoformate. Through the gas dispersion tube is added 10 grams of hydrogen chloride gas. With stirring, 200 ml methyl alcohol are added to the reaction mass maintaining the temperature at 45° C. The reaction mass is stirred for 15 minutes.

30 Grams of sodium carbonate is then added to the reaction mass and the reaction mass is stirred for another 10 minutes.

500 Ml water is added to the reaction mass. The organic phase is then separated from the aqueous phase and the organic phase is distilled on a 6" stone packed column yielding the following fractions:

| FRACTION NO. | VAPOR TEMP. (°C.) | LIQUID TEMP. (°C.) | VACUUM mm/Hg. PRESSURE | WEIGHT OF FRACTION (gms) |
|---|---|---|---|---|
| 1 | 87/90 | 100/100 | 15.0/15.0 | 16 |
| 2 | 95 | 100 | 15.0 | 32 |
| 3 | 95 | 99 | 15.0 | 41 |
| 4 | 95 | 99 | 15.0 | 51 |
| 5 | 92 | 99 | 14.0 | 39 |
| 6 | 76 | 89 | 5.0 | 232 |
| 7 | 77 | 89 | 5.0 | 220 |
| 8 | 75 | 97 | 3.0 | 216 |
| 9 | 72 | 107 | 3.0 | 36 |
| 10 | 65 | 170 | 1.8 | 15 |

FIG. 1 is the NMR spectrum for fraction 7 of the foregoing distillation containing the compound having the structure:

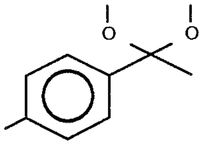

(Conditions: Field strength: 100 MHz; solvent: $CFCl_3$).

FIG. 2 is the infra-red spectrum for fraction 7 of the foregoing distillation containing the compound having the structure:

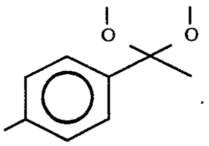

Bulked fractions 6–9 for the foregoing distillation have an intense substantive long lasting, sweet, animalic, musky and licorice aroma with floral, basil and ylang topnotes.

EXAMPLE II

Jasmine Perfume

The following mixture is prepared:

| INGREDIENTS | PARTS BY WEIGHT |
|---|---|
| Para Cresol | 1 |
| Acetyl Methyl Anthranilate | 20 |
| Farnesol | 4 |
| Cis-3-hexenyl benzoate | 30 |
| Nerolidol | 30 |
| Indole | 15 |
| Eugenol | 20 |
| Benzyl Alcohol | 40 |
| Methyl Linoleate | 40 |

-continued

| INGREDIENTS | PARTS BY WEIGHT |
|---|---|
| Jasmine Lactone | 20 |
| Dihydromethyl Jasmonate | 10 |
| Linalool | 150 |
| Benzyl Acetate | 400 |
| Abietyl Alcohol | 150 |
| Nor-methyl Jasmonate | 20 |
| Cis-Jasmone | 50 |

To this formulation 150 parts by weight of para-methylacetophenone dimethylacetal is added. The para-methylacetophenone dimethylacetal imparts to this intense jasmine formulation sweet, animalic, musky and licorice undertones with floral, basil and ylang topnotes. Accordingly, the perfume formulation can be described as having "a jasmine aroma with sweet, animalic, musky and licorice undertones and floral, basil and ylang topnotes".

EXAMPLE III

Perfumed Liquid Detergent

Concentrated liquid detergents (Lysine salt of n-dodecylbezene sulfonic acid as more specifically described in U.S. Pat. No. 3,948,818 issued on Apr. 6, 1976) with aromas as set forth in Table I below are prepared containing 0.10%, 0.15%, 0.20%, 0.30% and 0.40% of the perfume substances set forth in Table I below. They are prepared by adding and homogeneously mixing the appropriate quantity of perfume substance of Table I below in a liquid detergent. The detergents all possess excellent aromas as set forth in Table I below:

TABLE I

| PERFUME SUBSTANCE | AROMA PROFILE |
|---|---|
| Para-methylacetophenone dimethylacetal having the structure: 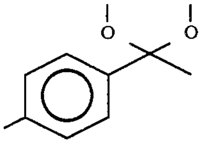 prepared according to Example I | A long lasting substantive aesthetically pleasing, sweet, animalic, musky and licorice aroma with floral, basil and ylang topnotes. |
| Perfume composition of Example II | A jasmine aroma with sweet, animalic, musky and licorice undertones and floral, basil and ylang topnotes. |

EXAMPLE IV

Preparation of a Cologne and Handkerchief Perfume

One of the perfume substances set forth in Table I of Example III is incorporated into colognes at concentrations of 2.0%, 2.5%, 3.0%, 3.5%, 4.0%, 4.5% and 5.0% in 80%, 85%, 90% and 95% aqueous food grade ethanol; and into handkerchief perfumes at concentrations of 15%, 20%, 25% and 30% (in 90% and 95% aqueous food grade ethanol solutions). Distinct and definitive aromas as set forth in Table I of Example III, supra, are imparted to the colognes and to the handkerchief perfumes at all levels indicated above.

EXAMPLE V

Preparation of Soap Composition

One hundred grams of soap chips prepared by chopping up a soap prepared as follows according to Japanese Pat. No. 79/28846 assigned to Kawaken Fine Chemicals Company:

"Fatty acid monoisopropanolamide ethoxylate 30 pts. and $P_2O_3$ 2.5 pts. are reacted and the product is combined with triethanolamine phosphate and a basic soap material and made into soap cakes"

are mixed with one gram of one of the perfume substances of Table I of Example III until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example III, supra.

EXAMPLE VI

Preparation of a Solid Detergent Composition

A detergent is prepared from the following ingredients according to Example I of Canadian Pat. No. 1,007,948 the specification for which is incorporated herein by reference:

| INGREDIENTS | PARTS BY WEIGHT |
|---|---|
| "Neodol 45-11" (a $C_{14}$—$C_{15}$ alcohol ethoxylated with 11 moles of ethylene oxide) | 12 |
| Sodium carbonate | 55 |
| Sodium citrate | 20 |
| Sodium sulfate, water and brighteners | q.s. |

This detergent is a phosphate free detergent. A total of 100 grams of this detergent is admixed (separately) with 0.15 grams of each of the perfume substances of Table I of Example III, supra. The detergent samples each have excellent aromas as set forth in Table I of Example III.

EXAMPLE VII

Utilizing the procedure of Example I at column 15 of U.S. Pat. No. 3,632,396 (the specification for which is incorporated by reference herein) a nonwoven cloth substrate useful as a drier added fabric softening article of manufacture is prepared wherein the substrate, the substrate coating and the outer coating and the perfuming material are as follows:

1. A water "dissolvable" paper ("Dissolvo Paper");
2. Adogen 448 (m.p. about 140° F.) as the substrate coating; and
3. An outer coating having the following formulation: (m.p. about 150° F.):
   57 percent $C_{20-22}$ HAPS
   22 percent isopropyl alcohol
   20 percent antistatic agent
   1 percent of one of the perfume substances (separately) as set forth in Table I of Example III, supra.

Fabric softening compositions prepared as set forth above having the aroma characteristics set forth in Table I of Example III, supra, consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate.

The aroma as set forth in Table I of Example III are imparted in a pleasant manner to the head space in the dryer on operation thereof using said dryer-added fabric softening nonwoven fabric.

EXAMPLE VIII

Liquid Washing Detergent

A liquid washing detergent with mild foaming action is prepared according to Japanese Patent No. 79/028847 wherein 12 weight percent of polyoxyethylene-2-butyl octyl ether sulphate having the formula $CH_3(CH_2)_5CH—(C_4H_9)CH_2O(CH_2O)_8SO_3K$ and 14 percent of dimethyl cetyl amine oxide and 12 percent dimethyl alkyl betaine and 0.4 percent of one of the perfume substances of Table I of Example III, supra. The resulting liquid washing detergents with mild foaming action have interesting aromas as set forth in Table I of Example III, supra.

What is claimed is:

1. A process for augmenting or enhancing the aroma of a perfume composition comprising the step of adding to said perfume composition, an aroma augmenting or enhancing amount of para-methylacetophenone dimethylacetal having the structure:

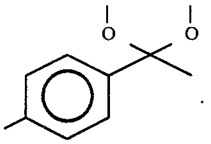

2. A process for augmenting or enhancing the aroma of a solid or liquid anionic, cationic, nonionic or zwitterionic detergent comprising the step of adding to said detergent, an aroma augmenting or enhancing quantity of para-methylacetophenone dimethylacetal having the structure:

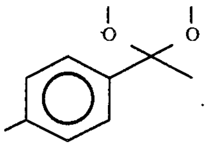

3. A process for augmenting or enhancing the aroma of a perfumed polymer comprising the step of adding to said perfumed polymer, an aroma augmenting or enhancing quantity of para-methylacetophenone dimethylacetal having the structure:

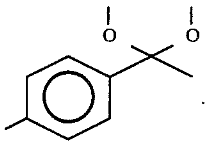

4. A process for augmenting or enhancing the aroma of a fabric softener composition or a drier-added fabric softener article comprising the step of adding to said fabric softener composition or drier-added fabric softener article, an aroma augmenting or enhancing quantity of para-methylacetophenone dimethylacetal having the structure:

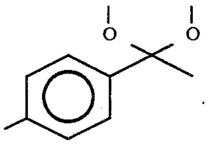

* * * * *